United States Patent
Blatter et al.

(10) Patent No.: US 9,394,328 B2
(45) Date of Patent: Jul. 19, 2016

(54) CRYSTALLINE DAPAGLIFLOZIN HYDRATE

(71) Applicant: SANDOZ AG, Basel (CH)

(72) Inventors: Fritz Blatter, Reinach (CH); Katharina Reichenbaecher, Rheinfelden (DE)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/360,583

(22) PCT Filed: Nov. 28, 2012

(86) PCT No.: PCT/EP2012/073783
§ 371 (c)(1),
(2) Date: May 23, 2014

(87) PCT Pub. No.: WO2013/079501
PCT Pub. Date: Jun. 6, 2013

(65) Prior Publication Data
US 2014/0323417 A1    Oct. 30, 2014

(30) Foreign Application Priority Data

Nov. 28, 2011 (EP) .................................... 11190866

(51) Int. Cl.
| | | |
|---|---|---|
| *C07H 15/04* | (2006.01) |
| *A01N 43/04* | (2006.01) |
| *A61K 31/70* | (2006.01) |
| *C07H 7/04* | (2006.01) |
| *C07D 309/10* | (2006.01) |

(52) U.S. Cl.
CPC ................ *C07H 7/04* (2013.01); *C07D 309/10* (2013.01)

(58) Field of Classification Search
CPC ................................ C07H 7/04; C07D 309/10
See application file for complete search history.

(56) References Cited

U.S. PATENT DOCUMENTS

| | | | |
|---|---|---|---|
| 6,515,117 B2 * | 2/2003 | Ellsworth et al. | 536/17.2 |
| 7,851,502 B2 * | 12/2010 | Bindra et al. | 514/460 |
| 7,919,598 B2 * | 4/2011 | Gougoutas et al. | 536/1.11 |
| 8,221,786 B2 * | 7/2012 | Bindra et al. | 424/452 |
| 8,361,972 B2 * | 1/2013 | Bindra et al. | 514/23 |
| 8,716,251 B2 * | 5/2014 | Bindra et al. | 514/23 |
| 8,871,264 B2 * | 10/2014 | Hallgren et al. | 424/464 |

FOREIGN PATENT DOCUMENTS

WO   WO 2008/002824 A1   1/2008

OTHER PUBLICATIONS

International Search Report, International Application No. PCT/EP2012/073783 mailing date Feb. 20, 2013.

* cited by examiner

*Primary Examiner* — Lawrence E Crane
(74) *Attorney, Agent, or Firm* — Arent Fox LLP

(57) ABSTRACT

A crystalline dapagliflozin hydrate and a process for obtaining the same is described.

15 Claims, 2 Drawing Sheets

Powder X-ray diffraction pattern of crystalline dapagliflozin hydrate (form A)

Raman spectrum of crystalline dapagliflozin hydrate (form A) in the wavenumber region from 100 to 1800 cm$^{-1}$ Powder X-ray diffraction pattern of crystalline dapagliflozin hydrate (form B)

CRYSTALLINE DAPAGLIFLOZIN HYDRATE

CROSS-REFERENCE TO RELATED APPLICATION

This application is a National Stage entry of International Application No. PCT/EP2012/073783, filed Nov. 28, 2012, which claims priority to European Application No. 11190866.1, filed Nov. 28, 2011, the entire specifications, claims and drawings of which are incorporated herewith by reference.

The present invention is directed to crystalline dapagliflozin hydrate and a process of obtaining the same.

The present invention relates to dapagliflozin being an inhibitor of sodium dependent glucose transporters found in the intestine and kidney (SGLT2) and to a method for treating diabetes, especially type II diabetes, as well as hyperglycemia, hyperinsulinemia, obesity, hypertriglyceridemia, Syndrome X, diabetic complications, atherosclerosis and related diseases, employing such C-aryl glucosides alone or in combination with one, two or more other type antidiabetic agent and/or one, two or more other type therapeutic agents such as hypolipidemic agents.

Approximately 100 million people worldwide suffer from type II diabetes (NIDDM—non-insulin-dependent diabetes mellitus), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney would be expected to aid in the normalization of plasma glucose levels, and perhaps body weight, by enhancing glucose excretion.

WO 03/099836 A1 refers to dapagliflozin having the structure according to formula 1.

formula 1

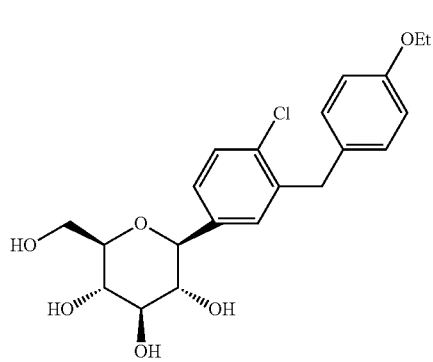

WO 03/099836 A1 discloses a route of synthesis on pages 8-10, whereby one major step is the purification of a compound of formula 2 formula 2

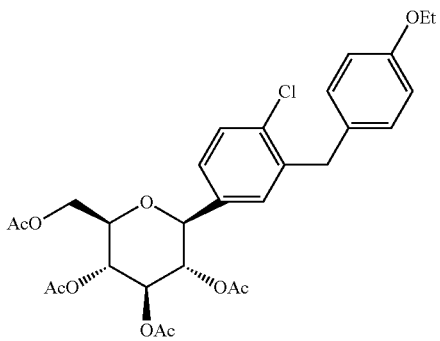

The compound of formula 2 provides a means of purification for providing a compound of formula 1 since it crystallizes. Subsequently the crystalline form of the compound of formula 2 can be deprotected and converted to dapagliflozin. Using this process, dapagliflozin is obtained as an amorphous glassy off-white solid containing 0.11 mol % of EtOAc. Crystallization of a pharmaceutical drug is usually advantageous as it provides means for purification also suitable for industrial scale preparation. However, for providing an active pharmaceutical drug a very high purity is required. In particular, organic impurities such as EtOAc either need to be avoided or further purification steps are needed to provide the drug in a pharmaceutically acceptable form, i.e. substantially free of organic solvents. Thus, there is the need in the art to obtain pure and crystalline dapagliflozin which is substantially free of organic solvents.

WO 2008/002824 A1 discloses several alternative solid forms of dapagliflozin, such as e.g. solvates containing organic alcohols or co-crystals with amino acids such as proline and phenylalanine. For instance, the document discloses crystalline dapagliflozin solvates which additionally contain water molecules (see e.g. Examples 3-6), but is silent about solid forms of dapagliflozin which do not contain impurities such as organic alcohols. As described above, it is desirable to provide the pharmaceutical active drug in a substantially pure form, otherwise triggering further expensive and time-consuming purification steps. In contrast, the document relates to dapagliflozin solvates where an alcohol and water are both incorporated into the crystal lattice. Hence, there is the need in the art to obtain pure and crystalline dapagliflozin suitable for pharmaceutical production.

WO 2008/116179 A1 refers to an immediate release pharmaceutical composition comprising dapagliflozin and propylene glycol. Propylene glycol is a chiral substance and (S)-propylene glycol used is very expensive. Consequently, also the immediate release pharmaceutical composition is more expensive.

Crystalline forms (in comparison to the amorphous form) often show desired different physical and/or biological characteristics which may assist in the manufacture or formulation of the active compound, to the purity levels and uniformity required for regulatory approval. As described above, it is desirable to provide the pharmaceutical active drug in a substantially pure form, otherwise triggering further expensive and time-consuming purification steps.

Moreover, the provision of further crystalline forms of a pharmaceutically useful compound offers an opportunity to improve the performance profile of a pharmaceutical product.

In particular, not all solid forms of a pharmaceutically useful compound are equally suited for development of a pharmaceutical dosage form. It is therefore desirable to widen the reservoir of materials a formulation scientist can select from, such that he can design a new dosage form of a drug having improved characteristics.

The technical problem underlying the present invention is the provision of a crystalline form comprising dapagliflozin and the provision of a process for obtaining the same in high yield and high purity.

It is therefore an object of the present invention to provide a cheap, easy-to-use and reproducible method capable of providing dapagliflozin in a substantially pure crystalline form. Accordingly, it is a further object of the present invention to provide dapagliflozin in a substantially pure crystalline form which is suited for pharmaceutical purposes. Furthermore, it would be desirable to provide a solid form of dapagliflozin showing improved physical and/or biological characteristics which may assist in the manufacture or formulation of the active compound, to the purity levels and/or uniformity required for regulatory approval.

The solid form of the present invention, in particular crystalline dapagliflozin hydrate, possesses improved pharmacological characteristics, for example, improved bioavailability, thus offering enhanced possibilities to modulate and design improved drug products.

The technical problem is solved by crystalline dapagliflozin hydrate.

The term "hydrate" as used herein designates a crystalline molecular compound in which water molecules are incorporated into the crystal lattice. Generally speaking, a hydrate thus designates a crystalline form of a molecular compound, whereby the only further molecules incorporated into the crystal lattice are water molecules.

In contrast to a hydrate, the term "solvate" as used herein designates a crystalline molecular compound in which molecules of the solvent(s) other than water are incorporated into the crystal lattice. Generally speaking, the solvent(s) incorporated into the crystal lattice may be an organic solvent (such as an alcohol, e.g. methanol, ethanol etc.), a mixture of at least two organic solvents or a mixture of an organic solvent and water.

Hence, the term "crystalline dapagliflozin hydrate" as used herein means a crystalline form of dapagliflozin containing water molecules combined in a definite ratio as an integral part of the crystal. Consequently, WO 2008/002824 A1 does not anticipate the subject matter of the present invention since said reference is directed to dapagliflozin solvates where an alcohol and water is incorporated into the crystal lattice.

Preferably, in the crystalline dapagliflozin hydrate the molar ratio of dapagliflozin and water is in the range of 1:1 to 1:6. In an even more preferred embodiment the molar ratio of dapagliflozin and water is in the range of 1:1 to 1:3, preferably, 1:1.5 to 1:2.5 and most preferred 1:2. Thus, a preferred embodiment of the present invention is crystalline dapagliflozin dihydrate.

Preferably, the crystalline dapagliflozin hydrate has an XRPD pattern with at least one characteristic peak (expressed in 2θ±0.2° 2θ(CuKα radiation)) at 9.2°, 12.0°, 16.1°, 16.4°, 18.4°, 24.8° and 30.0°, designated as form A. More preferably, the crystalline dapagliflozin hydrate has an XRPD pattern with characteristic peaks (expressed in 2θ±0.2° 2θ (CuKα radiation)) at 9.2°, 12.0°, 16.1°, 16.4°, 18.4°, 24.8° and 30.0°, designated as form A. Preferably, form A has an XRPD pattern with at least one characteristic peak (expressed in 2θ±0.2° 2θ (CuKα radiation)) at 9.2°, 11.7°, 12.0°, 16.1°, 16.4°, 18.4°, 20.1°, 24.8°, 26.0°, 30.0° and 32.6°. More preferably, form A has an XRPD pattern with characteristic peaks (expressed in 2θ±0.2° 2θ (CuKα radiation)) at 9.2°, 11.7°, 12.0°, 16.1°, 16.4°, 18.4°, 20.1°, 24.8°, 26.0°, 30.0° and 32.6°. Typically such an X-ray powder diffractogram is measured with copper K-alpha radiation. An X-ray powder diffractogram of a sample of form A is shown in FIG. 1 and the present invention, in a preferred embodiment, relates to form A displaying a XRPD pattern which is substantially in accordance with FIG. 1.

Preferably, the crystalline dapagliflozin hydrate form A has a FT-Raman spectrum comprising peaks at wavenumbers (expressed in ±2 cm$^{-1}$) of 2932, 1614, 1604, 1237, 1041, 844, 691, 638 and 107 cm$^{-1}$. An FT Raman spectrum of a sample of form A is shown in FIG. 2. In a preferred embodiment, form A is characterized by an FT Raman spectrum substantially in accordance with FIG. 2.

In a further preferred embodiment of the present invention the crystalline dapagliflozin has an XRPD pattern with at least one characteristic peak (expressed in 2θ±0.2° 2θ (CuKα radiation)) at 8.9°, 15.8°, 16.0°, 16.1°, 20.0° and 24.2° designated as form B. In a further preferred embodiment of the present invention the crystalline dapagliflozin has an XRPD pattern with characteristic peaks (expressed in 2θ±0.2° 2θ (CuKα radiation)) at 8.9°, 15.8°, 16.0°, 16.1°, 20.0° and 24.2° designated as form B. Preferably, form B has an XRPD pattern with at least one characteristic peak (expressed in 2θ±0.2° 2θ (CuKα radiation)) at 8.9°, 9.2°, 11.1°, 11.3°, 12.0°, 15.8°, 16.0°, 16.1°, 16.4°, 18.0°, 20.0°, 24.0°, 24.2°, 24.3°, 24.8°, 25.2° and 25.5°. More preferably, form B has an XRPD pattern with characteristic peaks (expressed in 2θ±0.2° 2θ (CuKα radiation)) at 8.9°, 9.2°, 11.1°, 11.3°, 12.0°, 15.8°, 16.0°, 16.1°, 16.4°, 18.0°, 20.0°, 24.0°, 24.2°, 24.3°, 24.8°, 25.2° and 25.5°. Typically such an X-ray powder diffractogram is measured with copper K-alpha radiation. An X-ray powder diffractogram of a sample of form B is shown in FIG. 3 and the present invention, in a preferred embodiment, relates to form B displaying a XRPD pattern which is substantially in accordance with FIG. 3.

Form B can be converted into form A. In order to obtain form A, a suspension of form B in water must be stirred. Subsequently, form A can be filtered off. Thus, form B is a useful intermediate for obtaining form A. Preferably, dapagliflozin hydrate form B is suspended in water, the resulting suspension is stirred for several hours, the suspension is subsequently filtered, and the wet cake is dried in air.

A further aspect of the present invention is above described crystalline dapagliflozin hydrate for use in the treatment of a disease. A further aspect of the present invention is above described crystalline dapagliflozin hydrate for use in the treatment of type II diabetes (NIDDM—non-insulin-dependent diabetes mellitus).

The present invention is also directed to a pharmaceutical composition comprising above described crystalline dapagliflozin hydrate and optionally one or more pharmaceutically acceptable excipients.

Preferably, the pharmaceutical composition is used in the treatment of type II diabetes (NIDDM—non-insulin-dependent diabetes mellitus).

The present invention is also directed to a process for obtaining above described crystalline dapagliflozin hydrate comprising the steps of:

a) providing a compound of formula 1 (INN: Dapagliflozin)

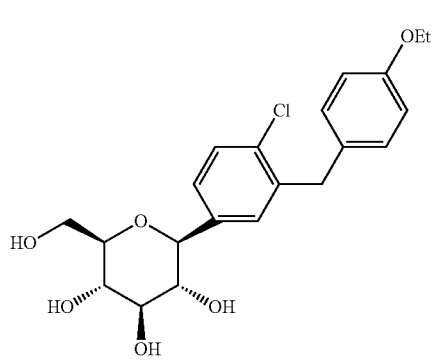

formula 1 in a suitable solvent or a mixture of solvents;
b) optionally adding a polyol to the mixture of step a);
c) optionally concentrating the composition of step b);
d) crystallizing;
e) optionally equilibrating the obtained suspension of step d); and
f) isolating the obtained precipitate.

In the context of the present invention the term "equilibrating" is used to express that the composition containing crystalline material is stirred until a thermodynamically equilibrium between solid and liquid phase is obtained.

Preferably, the present invention is directed to a process for obtaining above described crystalline dapagliflozin hydrate (preferably form A) comprising the steps of:

a) providing a compound of formula 1 (INN: Dapagliflozin)

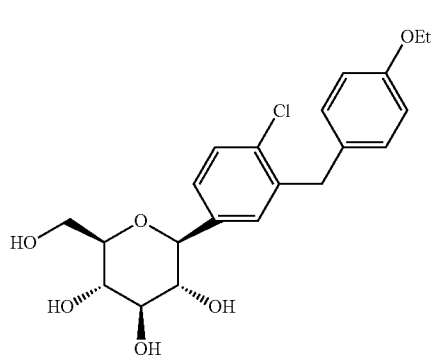

formula 1 in a suitable solvent or a mixture of solvents;
b) optionally adding a polyol to the mixture of step a);
c) optionally concentrating the composition of step b);
d) adding seed crystals of the desired form (preferably form A) and crystallizing;
e) optionally equilibrating the obtained suspension of step d); and
f) isolating the obtained precipitate.

In a further preferred embodiment, the present invention is directed to a process for obtaining above described crystalline dapagliflozin hydrate (preferably form A) comprising the steps of:

a) providing a compound of formula 1 (INN: Dapagliflozin)

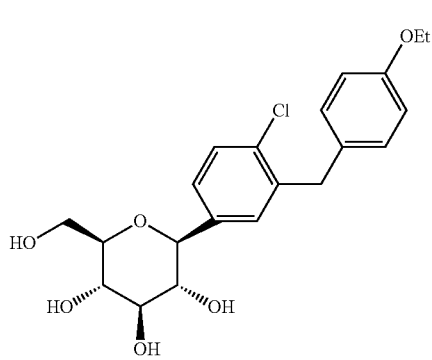

formula 1 in a suitable solvent or a mixture of solvents;
b) adding a polyol to the mixture of step a);
c) optionally concentrating the composition of step b);
d) crystallizing and optionally adding seed crystals of the desired form (preferably form A);
e) optionally equilibrating the obtained suspension of step d); and
f) isolating the obtained precipitate.

In the context of the present invention polyols are compounds comprising multiple, i.e. more than two hydroxyl functional groups. Preferably, hydroxyl groups are the only type of functional groups in the polyol.

Preferably, the molar ratio of the compound of formula 1 in step a) and the polyol of step b) is in the range from 1:0.1 to 1:3.

Even more preferred, the polyol is a sugar alcohol. A sugar alcohol is a hydrogenated form of carbohydrate, whose carbonyl group has been reduced to a primary or secondary hydroxyl group (hence the alcohol). Sugar alcohols have the general formula $H(HCHO)_{n+1}H$, whereas sugars have $H(HCHO)_n HCO$. Both disaccharides and monosaccharides can form sugar alcohols; however, sugar alcohols derived from disaccharides (e.g. maltitol and lactitol) are not entirely hydrogenated because only one aldehyde group is available for reduction.

Preferably, the sugar alcohol is selected from the group consisting of glycol, glycerol, erythritol, threitol, arabitol, xylitol, ribitol, mannitol, sorbitol, dulcitol, iditol, isomalt, maltitol, lactitol, polyglycitol and mixtures thereof. Most preferably, the polyol is selected from the group consisting of arabitol, xylitol, and mannitol.

Preferably, the solvent is selected from the group consisting of water, C1-C4 alcohols, a C3-C6 ketone, an ether or an acetic ester or mixtures thereof. In case a solvent mixture is used, preferably, water is present in said mixture. Even more preferred, the solvent is water or the amount of water in the solvent mixture is at least 50 weight-%.

Preferably, in step d) and/or e) seed crystals (preferably form A) are added.

In a further preferred embodiment, the present invention is directed to a process for providing seed crystals of crystalline dapagliflozin hydrate (preferably form A), comprising:

a) providing a compound of formula 1 (INN: Dapagliflozin)

formula 1 in a suitable solvent or a mixture of solvents, preferably water;
b) adding a sugar alcohol, preferably being selected from the group consisting of arabitol, xylitol, and mannitol, to the mixture of step a);
c) optionally, concentrating the composition of step b);
d) crystallizing; and
e) isolating the obtained precipitate.

In a further preferred embodiment, the present invention is directed to a process for providing form A of crystalline dapagliflozin hydrate, comprising:
a) providing a compound of formula 1 (INN: Dapagliflozin)

formula 1 in a suitable solvent or a mixture of solvents, preferably water;
b) optionally, adding a sugar alcohol, preferably being selected from the group consisting of arabitol, xylitol, and mannitol, to the mixture of step a);
c) optionally, concentrating the composition of step b);
d) adding seed crystals of the desired form, preferably of form A of crystalline dapagliflozin hydrate, and crystallizing; and
e) isolating the obtained precipitate.

Surprisingly, amorphous dapagliflozin can be purified with the process of the present invention. For instance amorphous dapagliflozin having a purity of 99.0% can be converted to crystalline dapagliflozin hydrate having a purity of 100% (see examples of the present application). Moreover, said crystalline dapagliflozin hydrate does not contain any additional solvent which is desirable. Thus, the process of purifying dapagliflozin according to the present invention is superior compared with the process of WO 03/099836 A1.

Additionally, the dapagliflozin hydrate obtained is crystalline which is advantageous with respect to the formulation of a pharmaceutical composition. The use of expensive diols such as (S)-propanediol for obtaining an immediate release pharmaceutical composition as disclosed in WO 2008/116179 A1 can be avoided.

EXPERIMENTAL

Figure 1:
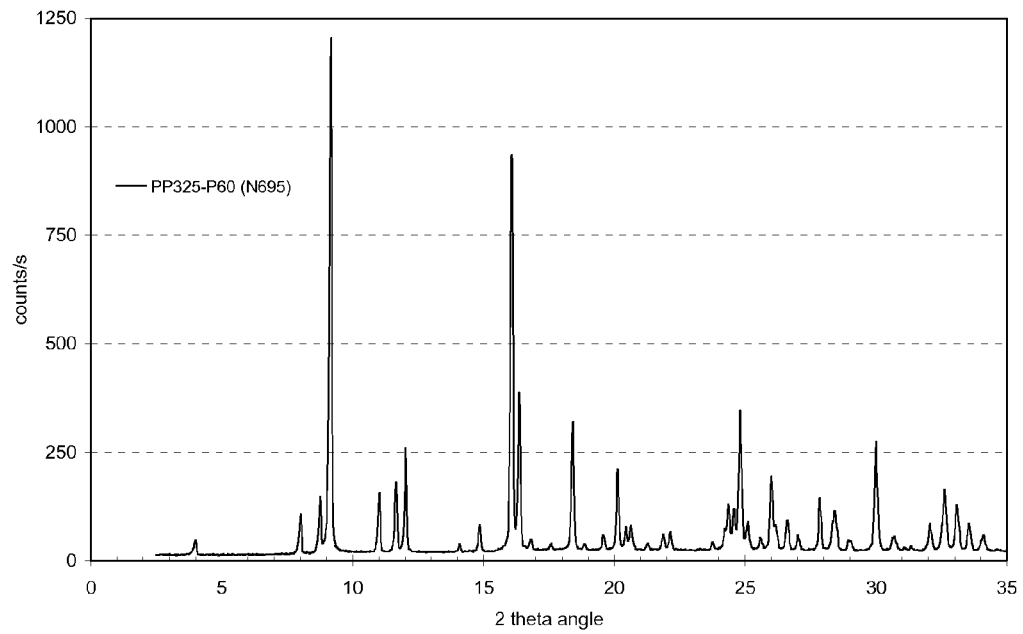
FIG. 1 shows an example of an X-ray powder diffractogram of crystalline form A, in accordance with aspects of the present invention.

Powder X-Ray Diffraction (PXRD):
The measurements were carried out with a Bruker D8 Advance powder X-ray diffractometer using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The samples were prepared without any special treatment other than the application of slight pressure to get a flat surface. Silicon single crystal sample holders of either 0.5 mm or 0.1 mm depth and 12 mm cavity diameter were used. The tube voltage and current were 40 kV and 40 mA, respectively. The X-ray diffractometer is equipped with a LynxEye detector. A variable divergence slight was used with a 3° window. The step size was 0.02° 2θ with a step time of 37 seconds. The samples were rotated at 0.5 rps during the measurement.

TG-FTIR:
Thermogravimetry coupled with Fourier Transform Infrared Spectroscopy (TG-FTIR): TG-FTIR was performed on a Netzsch Thermo-Microbalance TG 209, which is coupled to a Bruker FT-IR Spectrometer Vector 22. The measurements were carried out with aluminum crucibles with a micro pinhole under a nitrogen atmosphere and at a heating rate of 10° C./min over the range 25-250° C.

FT-Raman Spectroscopy:
Raman spectra were recorded using a Bruker RFS100 Raman spectrometer equipped with a germanium detector and a Nd:YAG laser with an excitation wavelength of 1064 nm. A few milligrams of material were pressed into aluminum sample holders. Spectra in the range of 50-3500 $cm^{-1}$ and with a resolution of 2 $cm^{-1}$ were measured with a laser power of 100 mW. 64 scans were accumulated.

$^1$H-NMR Spectroscopy:
$^1$H-NMR spectra were recorded using a Bruker DPX300 instrument. Deuterated methanol was used as the solvent.

HPLC Method:
HPLC measurements were performed with an Agilent 1100 series instrument equipped with a UV-vis detector set to 240 nm according to the following method: Column: Ascentis Express RP-Amide 4.6×150 mm, 2.7 mm, Column temperature: 25° C.
Eluent A: 0.1% formic acid in water
Eluent B: 0.1% formic acid in acetonitrile Injection volume: 3 mL
Flow: 0.7 mL/min
Gradient:

| Time [min] | [%] B |
|---|---|
| 0.0 | 25 |
| 25.0 | 65 |
| 26.0 | 70 |
| 29.0 | 70 |
| 29.5 | 25 |
| 35.0 | 25 |

Example 1

Preparation of Seed Crystals of Form A 50 mg of amorphous dapagliflozin is suspended in 3 ml water and heated to 80° C. to this mixture is added 18.6 mg L-(−)-arabitol (Sigma Aldrich # A3506) in 0.5 ml water. An emulsion is formed which is cooled to 5° C. at a rate of 2° C. per hour. At this temperature the mixture is stirred for about 20 hours or until crystals can be detected by light microscopy. After crystallization the suspension is filtered off and the solid product (after drying in air at room temperature for about one hour at a relative humidity of about 50%) is investigated by powder X-ray diffraction and $^1$H-NMR spectroscopy. $^1$H-NMR shows that the obtained crystalline solid contains dapagliflozin and water; whereas PXRD shows that crystalline form A is obtained.

Example 2

Preparation of Seed Crystals of Form A 50 mg of amorphous dapagliflozin is suspended in 3 ml water and heated to 80° C. to this mixture is added 22.2 mg D-mannitol (Riedel-deHaen #33440) in 0.5 ml water. An emulsion is formed which is cooled to 5° C. at a rate of 2° C. per hour. At this temperature the mixture is stirred for about 20 hours or until crystals can be detected by light microscopy. After crystallization the suspension is filtered off and the solid product (after drying in air at room temperature for about one hour at a relative humidity of about 50%) is investigated by powder X-ray diffraction and $^1$H-NMR spectroscopy. $^1$H-NMR shows that the obtained crystalline solid contains dapagliflozin and water; whereas PXRD shows that crystalline form A is obtained.

Example 3

Preparation of Seed Crystals of Form a 50 mg of amorphous dapagliflozin is suspended in 3 ml water and heated to 80° C. To this mixture 18.6 mg xylitol (Sigma Aldrich # X3375) in 0.5 ml water is added. An emulsion is formed which is cooled to 5° C. at a rate of 2° C. per hour. At this temperature the mixture is stirred for about 20 hours or until crystals can be detected by light microscopy. After crystallization the suspension is filtered off and the solid product (after drying in air at room temperature for about one hour at a relative humidity of about 50%) is investigated by powder X-ray diffraction and H-NMR spectroscopy. $^1$H-NMR shows that the obtained crystalline solid contains dapagliflozin and water; whereas PXRD shows that crystalline form A is obtained.

Example 4

Figure 2:
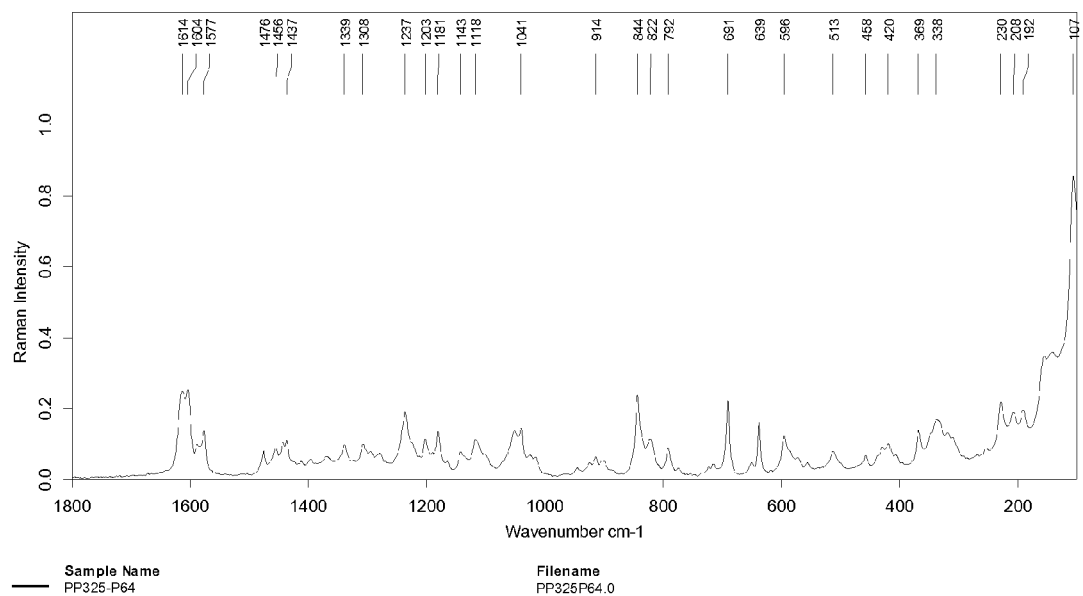
FIG. 2 shows an example of a Raman spectrum of crystalline form A, in accordance with aspects of the present invention.

Preparation of Crystalline Form A 156 mg of amorphous dapagliflozin is suspended in 22 ml water and heated to about 80° C. with a laboratory heat gun. The stirred emulsion is cooled to room temperature and about 10 mg of seed crystals according to example 1 are added. After further cooling to 5° C. the suspension is stirred at 5° C. for three days (or until crystalline material can be detected by light microscopy) before the solid product is separated by filtration. After drying under vacuum (10 mbar) at room temperature for 30 minutes the solid is investigated by powder X-ray diffraction and $^1$H-NMR spectroscopy. H-NMR shows that the obtained crystalline solid contains dapagliflozin and water; whereas PXRD shows that crystalline form A is obtained. The PXRD pattern of this form is shown in FIG. 1 and the peak locations are provided in table 1. Further investigation by Raman spectroscopy reveals a characteristic Raman spectrum as shown in FIG. 2 with peak locations as shown in table 2.

TABLE 1

Powder X-ray diffraction peak locations and qualitative relative intensities for dapagliflozin hydrate form A

| Angle 2θ | d-value [Å] | Intensity (qualitative) |
|---|---|---|
| 4.0 | 22.1 | vw |
| 8.0 | 11.0 | w |
| 8.8 | 10.1 | w |
| 9.2 | 9.6 | vs |
| 11.0 | 8.0 | w |
| 11.7 | 7.6 | m |
| 12.0 | 7.3 | m |
| 14.1 | 6.3 | vw |
| 14.9 | 5.96 | w |
| 16.1 | 5.51 | vs |
| 16.4 | 5.41 | s |
| 16.8 | 5.27 | vw |
| 17.6 | 5.04 | vw |
| 18.4 | 4.82 | s |
| 18.9 | 4.70 | vw |
| 19.6 | 4.53 | vw |
| 20.1 | 4.41 | m |
| 20.4 | 4.34 | w |
| 20.6 | 4.30 | w |
| 21.3 | 4.17 | vw |
| 21.9 | 4.06 | vw |
| 22.1 | 4.01 | w |
| 23.8 | 3.74 | vw |
| 24.2 | 3.67 | w |
| 24.4 | 3.65 | w |
| 24.6 | 3.62 | w |
| 24.8 | 3.58 | s |
| 25.1 | 3.54 | w |
| 25.6 | 3.48 | vw |
| 26.0 | 3.42 | m |
| 26.2 | 3.40 | w |
| 26.6 | 3.35 | w |
| 27.0 | 3.30 | vw |
| 27.9 | 3.20 | w |
| 28.3 | 3.15 | w |
| 28.4 | 3.14 | w |
| 30.0 | 2.98 | s |
| 32.1 | 2.79 | w |
| 32.6 | 2.74 | m | vw = very weak, w = weak, m = medium, s = strong, vs = very strong

TABLE 2

Raman peak locations for dapa hydrate form A

| wavenumber | relative intensity (arbitrary units) |
|---|---|
| 3074 | 6.3 |
| 2988 | 1.8 |
| 2932 | 10.4 |
| 2891 | 3.4 |
| 1614 | 1.8 |
| 1604 | 19.5 |
| 1577 | 6.2 |
| 1476 | 3.4 |
| 1456 | 1.9 |
| 1437 | 6.1 |
| 1339 | 3.8 |
| 1308 | 4.4 |
| 1237 | 14.1 |
| 1203 | 3.7 |
| 1181 | 7.1 |
| 1143 | 2.8 |
| 1118 | 6.4 |
| 1041 | 10.1 |
| 914 | 4 |
| 844 | 17.8 |
| 822 | 2.6 |
| 792 | 4.9 |
| 691 | 16.5 |
| 638 | 11.1 |
| 596 | 7.8 |
| 513 | 3.9 |
| 458 | 2.4 |
| 420 | 4.7 |
| 369 | 4.4 |
| 338 | 9.2 |
| 229 | 6.6 |
| 208 | 2.8 |
| 192 | 3.8 |
| 107 | 67.3 |

Example 5

Preparation of Crystalline Form A 1.5 gram of amorphous dapagliflozin is suspended in 60 ml water and heated to about 80° C. with a laboratory heat gun for a short time. The stirred emulsion is cooled to room temperature and about 50 mg of seed crystals according to example 1 are added. Then the suspension is stirred at room temperature for three days (or until crystalline material can be detected by light microscopy) before the solid product is separated by filtration. The wet cake after filtration is stored over a relative humidity of 75%, and then investigated by powder X-ray diffraction and H-NMR spectroscopy. $^1$H-NMR shows that the obtained crystalline solid contains dapagliflozin and water; whereas PXRD shows that crystalline form A is obtained. The PXRD pattern of this form is shown in FIG. 1 and the peak locations are provided in table 1.

Example 6

Figure 3:
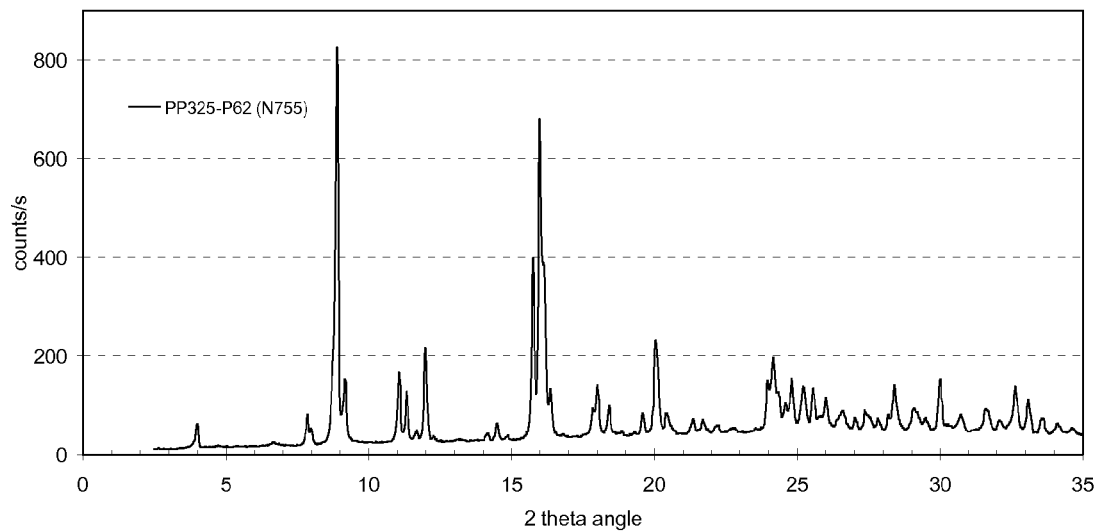
FIG. 3 shows an example of an X-ray powder diffractogram of crystalline form B, in accordance with aspects of the present invention.

Preparation of Crystalline Form B 1.0 gram of amorphous dapagliflozin is suspended in 140 ml water and heated to about 80° C. with a laboratory heat gun for a short time. The stirred emulsion is cooled to room temperature and then exposed to ultrasound in a standard laboratory ultrasound bath for about two minutes, whereby about 50 mg of seed crystals obtained according to example 5 are added. Then the suspension is further cooled to 5° C. and stirred for two days (or until crystalline material can be detected by light microscopy) before the solid product is separated by filtration. The wet cake after filtration is stored over a relative humidity of 31% for about 24 hours, and then investigated by powder X-ray diffraction and $^1$H-NMR spectroscopy. $^1$H-NMR shows that the obtained crystalline solid contains daps and water; whereas PXRD shows that crystalline form B is obtained. The PXRD pattern of this form is shown in FIG. 3 and the peak locations are provided in table 3.

TABLE 3

Powder X-ray diffraction peak locations and qualitative relative intensities for dapagliflozin hydrate form B

| Angle 2θ | d-value [Å] | Intensity (qualitative) |
|---|---|---|
| 4.0 | 22.1 | w |
| 7.9 | 11.2 | w |
| 8.0 | 11.0 | w |
| 8.9 | 9.9 | vs |
| 9.2 | 9.6 | m |
| 11.1 | 8.0 | m |
| 11.3 | 7.8 | m |
| 11.7 | 7.6 | w |
| 12.0 | 7.4 | m |
| 12.3 | 7.2 | vw |
| 14.2 | 6.3 | w |
| 14.5 | 6.11 | w |
| 14.9 | 5.96 | vw |
| 15.8 | 5.62 | s |
| 16.0 | 5.54 | vs |
| 16.1 | 5.50 | s |
| 16.4 | 5.41 | m |
| 17.8 | 4.97 | w |
| 18.0 | 4.92 | m |
| 18.4 | 4.81 | w |
| 18.9 | 4.70 | w |
| 19.6 | 4.53 | w |
| 20.0 | 4.43 | m |
| 20.4 | 4.34 | w |
| 21.4 | 4.16 | w |
| 21.7 | 4.09 | w |
| 22.2 | 4.00 | w |
| 22.8 | 3.90 | w |
| 24.0 | 3.71 | m |
| 24.2 | 3.68 | m |
| 24.3 | 3.66 | m |
| 24.6 | 3.62 | w |
| 24.8 | 3.58 | m |
| 25.2 | 3.53 | m |
| 25.5 | 3.48 | m |
| 26.0 | 3.43 | w |
| 26.4 | 3.37 | w |
| 26.6 | 3.35 | w |
| 27.0 | 3.30 | w | vw = very weak, w = weak, m = medium, s = strong, vs = very strong

Example 7

Water Content of Crystalline Hydrate Form A 145 mg of crystalline hydrate form A according to example 4 is stored under a relative humidity of 60% (in an open container) for two weeks. Then the stored sample is investigated by PXRD and TG-FTIR. PXRD shows that form A is retained whereas TG-FTIR reveals a mass loss of about 9% which is attributable to loss of water. Therefore, we conclude that in equilibrium with a water activity of about 0.6 the crystalline form A contains about 2 mol water per mol dapagliflozin, i.e. it is essentially a dihydrate.

Example 8

Purification by Crystallization

The purity in area % of amorphous dapagliflozin determined by HPLC is 99.8% (by the method provided in the experimental section). 156 mg of the amorphous dapagliflozin is suspended in 22 ml water and heated to about 80° C. with a laboratory heat gun. The stirred emulsion is cooled to room temperature and about 10 mg of seed crystals according to example 1 are added. After further cooling to 5° C. the suspension is stirred a 5° C. for three days (or until crystalline material can be detected by light microscopy) before the solid product is separated by filtration. After drying under vacuum (10 mbar) at room temperature for 30 minutes the solid is investigated by powder X-ray diffraction which confirms that crystalline form A is obtained. Further the obtained crystalline sample is tested with respect to chemical purity by the same HPLC method. A purity of 100% is found; i.e. all impurities are removed.

Example 9

Purification by Crystallization

The purity in area % of amorphous dapagliflozin determined by HPLC is 99.0% (by the method provided in the experimental section). 1.0 gram of this amorphous sample is suspended in 140 ml water and heated to about 80° C. with a laboratory heat gun for a short time. The stirred emulsion is cooled to room temperature, then exposed to ultrasound in a standard laboratory ultrasound bath for about two minutes, whereby about 50 mg of seed crystals obtained according to example 5 are added. Then the suspension is further cooled to 5° C. and stirred for two days (or until crystalline material can be detected by light microscopy) before the solid product is separated by filtration. The wet cake after filtration is stored over a relative humidity of 31% for about 24 hours, and then investigated by powder X-ray diffraction and $^1$H-NMR spectroscopy. $^1$H-NMR shows that the obtained crystalline solid contains dapagliflozin and water, whereas PXRD shows that crystalline dapagliflozin is obtained. A further test of the solid crystalline sample by the same HPLC method shows that the chemical purity 100%; i.e. all impurities were removed by crystallization.

Example 10

Conversion of Form B into Form A

About 200 mg of dapagliflozin hydrate form B is suspended in 2 ml water and the resulting suspension is stirred at 5° C. for 24 hours. Thereafter the suspension is filtered, the wet cake dried in air for about 30 minutes and then investigated by powder X-ray diffraction which confirms that crystalline form A is obtained.

Example 11

Purification by Crystallization

About 11 g of amorphous dapagliflozin is suspended in 1 L of water. The suspension is heated to 50° C. and stirred for 3 h. After addition of seed crystals of Form A, the sample is cooled to 5° C. with 10° C./h and stirred for about three days at 5° C. The suspension is filtered and the solid is stored for three days at 43% r.h. (over saturated solution of $K_2CO_3$).

The powder pattern of the solid corresponds to that of form A.

Investigation by HPLC reveals a purity of the obtained crystalline dapagliflozin form A of approximately 100%.

Example 12

About 101 mg of amorphous dapagliflozin was suspended in 2.0 ml water. This mixture was stirred at room temperature for about one week. Visual inspection reveals that upon shaking the vial an emulsion was formed and that no crystallization of the amorphous material has occurred. Then about 40 mg of vanilline was added and stirring at room temperature was continued for 25 days. However, after that time no crystalline material could be observed.

In a further approach, about 150 mg amorphous dapagliflozin was dissolved in 0.5 ml isopropanol and 2.0 ml water was added to the solution. An emulsion was formed which was stirred at room temperature for three days. No crystalline material was observed by visual inspection and light microscopy.

The invention claimed is:

1. Crystalline dapagliflozin hydrate.

2. The crystalline dapagliflozin hydrate of claim 1, wherein the molar ratio of dapagliflozin and water is in the range of 1:1 to 1:6.

3. The crystalline dapagliflozin hydrate of claim 1, which has an XRPD pattern with at least one characteristic peak (expressed in 2θ±0.2° 2θ (CuKα radiation)) at 9.2°, 12.0°, 16.1°, 16.4°, 18.4°, 24.8° and 30.0°, and which is designated as form A.

4. The crystalline dapagliflozin hydrate according to claim 3, which has a FT-Raman spectrum comprising peaks at wavenumbers (expressed in ±2 cm$^{-1}$) of 2932, 1614, 1604, 1237, 1041, 844, 691, 638 and 107 cm$^{-1}$.

5. The crystalline dapagliflozin hydrate of claim 1, which has an XRPD pattern with at least one characteristic peak (expressed in 2θ±0.2° 2θ (CuKα radiation)) at 8.9°, 15.8°, 16.0°, 16.1°, 20.0° and 24.2° and which is designated as form B.

6. A process for obtaining the crystalline form according to claim 1 comprising the steps of:
   a) providing a compound of formula 1 (INN: Dapagliflozin)

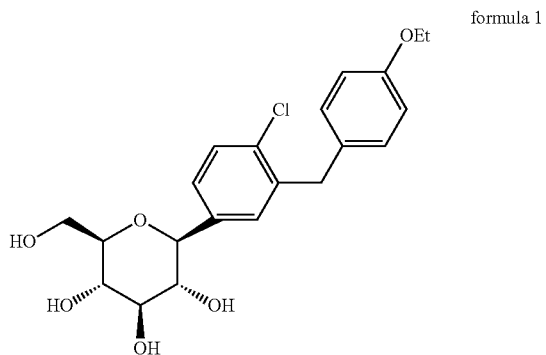 [SMILES: CCOc1ccc(Cc2cc([C@@H]3O[C@H](CO)[C@@H](O)[C@H](O)[C@H]3O)ccc2Cl)cc1]

formula 1 in a suitable solvent or a mixture of solvents;
   b) optionally adding a polyol to the mixture of step a);
   c) optionally concentrating the composition of step b);
   d) crystallizing;
   e) optionally equilibrating the obtained suspension of step d); and
   f) isolating the obtained precipitate.

7. The process according to claim 6, wherein the molar ratio of the compound of formula 1 in step a) and the polyol of step b) is in the range from 1:0.1 to 1:3.

8. The process according to claim 6, wherein the polyol is a sugar alcohol.

9. The process according to claim 8, wherein the sugar alcohol is selected from the group consisting of glycol, glycerol, erythritol, threitol, arabitol, xylitol, ribitol, mannitol, sorbitol, dulcitol, iditol, isomalt, maltitol, lactitol, polyglycitol and mixtures thereof.

10. The process according to claim 6, wherein the solvent is selected from the group consisting of water, C1-C4 alcohols, a C3-C6 ketone, an ether, an acetic ester and mixtures thereof.

11. The process according to claim 6 wherein the solvent is water or wherein the amount of water in the solvent mixture is at least 50 weight-%.

12. The process according to claim 6 wherein in step d) and/or e) seed crystals are added.

13. A pharmaceutical composition comprising crystalline dapagliflozin hydrate according to claim 1 and optionally one or more pharmaceutically acceptable excipients.

14. A method of treating type II diabetes (NIDDM—non-insulin-dependent diabetes mellitus) comprising administering to a subject in need thereof, a therapeutically effective amount of the pharmaceutical composition of claim 13.

15. A method of making crystalline dapagliflozin hydrate form A, comprising stirring a suspension of crystalline dapagliflozin hydrate form B in water and filtering off form A.

\* \* \* \* \*